US006830563B1

(12) United States Patent
Singer

(10) Patent No.: US 6,830,563 B1
(45) Date of Patent: Dec. 14, 2004

(54) SYRINGE TIP PROVIDING NONLAMINAR SPIRAL FLOW AND METHOD OF USE FOR FLUSHING CATHETERS

(76) Inventor: Scott Singer, 6811 Victoria Dr., Tuscaloosa, AL (US) 35405

(*) Notice: Subject to any disclaimer, the term of this patent is extended or adjusted under 35 U.S.C. 154(b) by 92 days.

(21) Appl. No.: 10/277,524

(22) Filed: Oct. 22, 2002

Related U.S. Application Data

(62) Division of application No. 09/939,381, filed on Aug. 24, 2001, now abandoned.

(51) Int. Cl.$^7$ ................................................ A61M 5/00
(52) U.S. Cl. ....................................... 604/181; 604/187
(58) Field of Search ................................ 604/181, 183, 604/187, 218, 235, 246, 247, 264, 266, 267, 275, 30, 35

(56) References Cited

U.S. PATENT DOCUMENTS

| | | |
|---|---|---|
| 3,675,891 A | 7/1972 | Reynolds et al. |
| 4,210,178 A | 7/1980 | Morse et al. |
| 4,228,802 A * | 10/1980 | Trott ........................... 128/349 |
| 4,245,636 A | 1/1981 | Sparks et al. |
| 4,291,702 A | 9/1981 | Cole et al. |
| 4,300,571 A | 11/1981 | Waldbillig |
| 4,341,224 A | 7/1982 | Stevens |
| 4,414,999 A | 11/1983 | Basta |
| 4,497,468 A | 2/1985 | Hubbard et al. |
| D279,407 S | 6/1985 | Hubbard |
| 4,624,662 A | 11/1986 | Le |
| 4,645,496 A | 2/1987 | Oscarsson |
| 4,954,129 A | 9/1990 | Giuliani et al. |
| 5,171,230 A | 12/1992 | Eland et al. |
| 5,279,280 A * | 1/1994 | Bacich et al. .................. 128/6 |
| 5,334,153 A | 8/1994 | McIntyre et al. |
| 5,549,548 A | 8/1996 | Larsson |
| 5,578,002 A | 11/1996 | Slettenmark |
| 5,624,662 A | 4/1997 | Unger et al. |
| 5,662,585 A * | 9/1997 | Willis et al. ................ 600/104 |

OTHER PUBLICATIONS

Macklin, Denise, Turbulent Flow and Catheter Residue, *JVAN*, Summer 1993, p14, vol. 3 No. 3.
Moureau, Nancy, Training for Turbulence, JVAD Fall 2000 *Practical Access insert*, p2.
Moureau, Nancy, Practicing Prevention with Implanted Ports, JVAD, Fall 1999, p30.
Moureau, Nancy; McKinnon, Barbara Thompson; Douglas, Claudia M., Multidisciplinary management of Thrombotic Catheter Occlusions in Vascular Access devices, *JVAD*, Summer 1999, 22.
Berger, Loretta, The Effects of Positive Pressure Devices on Catheter Occlusions, *JVAD*, Winter 2000, p31.

* cited by examiner

*Primary Examiner*—Long V. Le
*Assistant Examiner*—Ann Y. Lam
(74) *Attorney, Agent, or Firm*—Lanier Ford Shaver & Payne P.C.

(57) ABSTRACT

A syringe tip for generating nonlaminar spiral flow to flush indwelling vascular access devices, eliminating the need for start-stop flushing. The nonlaminar spiral flow is generated by spiral elements on the inner surface of the syringe tip.

7 Claims, 17 Drawing Sheets

6,830,563 B1

SYRINGE TIP PROVIDING NONLAMINAR SPIRAL FLOW AND METHOD OF USE FOR FLUSHING CATHETERS

This application is a division of U.S. patent application Ser. No. 09/939,381, filed Aug. 24, 2001, now abandoned.

BACKGROUND OF THE INVENTION

1. Field of the Invention

This invention relates to devices for flushing indwelling vascular catheters, and more particularly to syringe tips that create vortex or helical flow of flushing media to dislodge accumulated debris from the tip of the indwelling catheter.

2. Background of the Invention

Vascular indwelling catheters or vascular access devices are used to inject medication, withdraw blood, or monitor functions within the blood vessel such as blood pressure and heart rate. The operation of catheters is often compromised or completely prevented by the occurrence of thrombus formation. Thrombosis is the development of a blood clot within a vessel and/or a catheter. Immediately after a catheter or other vascular access device is inserted into a blood vessel, a coagulation cascade begins. Platelets and white blood cells attach to the catheter surfaces. As the platelets begin to aggregate, fibrin strands form to cover the foreign object. The types of thrombotic occlusions that occur in indwelling catheters are intraluminal thrombus, mural thrombus, fibrin tail or flap, and fibrin sheath or sleeve.

Intraluminal thrombi develop when blood enters the lumen of the catheter. Mural thrombi develop when the tip of the catheter causes injury to the inner vascular wall. A mural thrombus is formed when the fibrin from the vessel wall injury attaches to the fibrin building on the catheter surface. The adherence of fibrin, blood cells, and platelets to the end or tip of a catheter is called a fibrin tail or flap. As the tail or flap attached to the catheter sticks out into the blood stream, more cells and other blood products become deposited onto the tail. A persistent withdrawal occlusion is caused by the fibrin flap acting as a one-way valve, allowing the catheter to flush easily, but not allowing blood to be aspirated. A fibrin sheath or sleeve is formed from adherence of fibrin to the external surfaces of the catheter. The sleeve may cover the terminal tip of the catheter, and extend up the entire length of the catheter, also causing persistent withdrawal occlusion.

The purpose of flushing is to clean the accumulated residue from the internal lumen of the catheter or from the catheter tip. The common practice is to create a turbulent flow during flushing to promote a "scrubbing" effect in the lumen and at the tip of the catheter. Turbulent flow is usually provided by pulsative flushing. This technique utilizes a "start-stop" method that produces turbulence within the catheter lumen, reducing the potential for material to adhere to the catheter.

This "start-stop" turbulent positive pressure flushing is difficult to perform effectively and must be performed in narrowly prescribed ways. Notwithstanding training and practice, the turbulence generated is random and dependent upon the internal diameter of the catheter and rate of the flow of the flushing media, in addition to other factors, such as the time interval between starting and stopping. Furthermore, because the turbulence by this method is generally not uniform across the internal diameter of the catheter, turbulent forces upon opposing internal walls of the catheter may be unequal, producing a whip-like effect or oscillations at the catheter tip. If the catheter tip moves with force, it can cause damage to the inner lining of the blood vessel wall leading to increased thrombus formation.

The present invention overcomes these problems of the relatively unpredictable results of start-stop flushing by providing a syringe tip that produces uniform predictable nonlaminar flow. This flow is in the form of a controlled uniform helical spiral or vortex flow, which effectively scrubs the debris from the lumens and tips of indwelling vascular catheters and related devices, avoiding the necessity of using the relatively crude and uncontrolled method of pulsatile flushing.

SUMMARY OF THE INVENTION

The present invention is a syringe tip that produces a nonlaminar helical or spiral flow of liquid as the liquid is injected through the tip with a syringe. When the syringe tip is inserted into the proximal end of a catheter, the spiral flow is transmitted along the length of the catheter whereby the spiral flow can scrub or dislodge blood deposits from the catheter lumen and catheter tip. The spiral or helical flow is produced by spiral elements on and/or in the inner wall or in the lumen of the syringe tip. The spiral flow created by the syringe tip makes the syringe tip useful for flushing vascular catheters without having to use the less reliable method of high pressure start-stop flushing.

An advantage of the present invention is that it provides a syringe tip that creates nonlaminar spiral flow of catheter flushing media.

Another advantage of the present invention is that it can be used to dislodge blood-derived deposits from the catheter lumen and/or catheter tip.

Another advantage of the present invention is that it produces effective flushing of vascular catheters without producing a random turbulent flow, thereby avoiding oscillations at the catheter tip which can damage the inner wall of a blood vessel.

Another advantage of the present invention is that the syringe tip can be permanently or removably attached to a syringe.

Another advantage of the present invention is that it requires no special training or practice for use in flushing vascular catheters.

Another advantage of the present invention is that it is simple and inexpensive to construct.

Another advantage of the present invention is it's dual function: flushing vascular catheters and use in all other nonvascular syringe applications.

DETAILED DESCRIPTION OF THE PREFERRED EMBODIMENTS

While the following description details the preferred embodiments of the present invention, it is to be understood that the invention is not limited in its application to the details of construction and arrangement of parts illustrated in the accompanying drawings, since the invention is capable of other embodiments and of being practiced in various ways.

Figure 1:
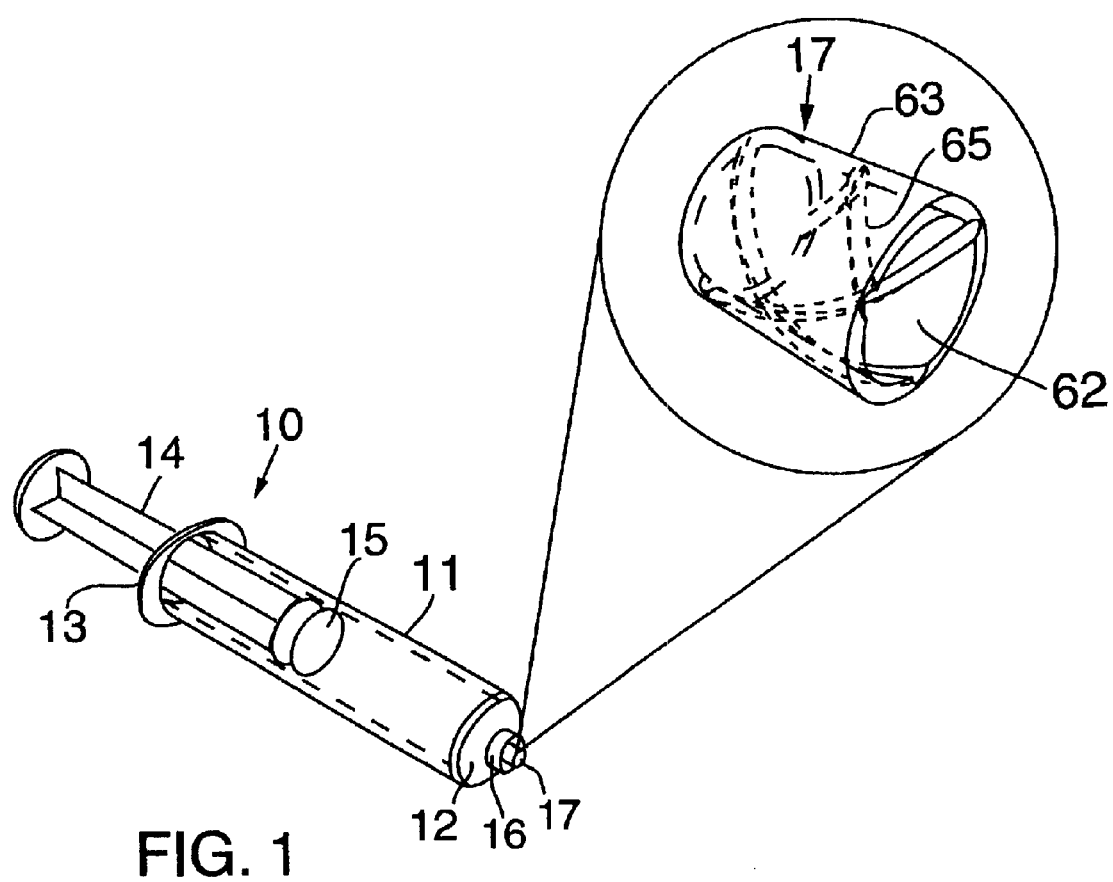
FIG. 1 shows a typical syringe used for flushing catheters but having the syringe tip of the present invention, illustrating the helical or spiral elements on the inner surface of the syringe tip.

FIG. 1 shows a typical syringe 10 known in the art, which can be used for flushing. The syringe has a cylindrical barrel 11 having a distal end 12 and a proximal end 13. The syringe has a plunger 14 with a piston head 15 which forces liquid out of distal end 12. Many syringes of this type have luer fittings 16 which contain syringe tip 17. Syringe tip 17 of the present invention is shown in an enlarged view to illustrate the spiral elements 65 on inner surface 62. The syringe tip 17 of the present invention has a circular inner bore defined by inner surface 62 and an outer surface 63. The syringe tip of the present invention can be constructed as a permanent tip of a syringe or can be constructed as an adaptor to fit over the standard tip of a syringe.

Figure 2:
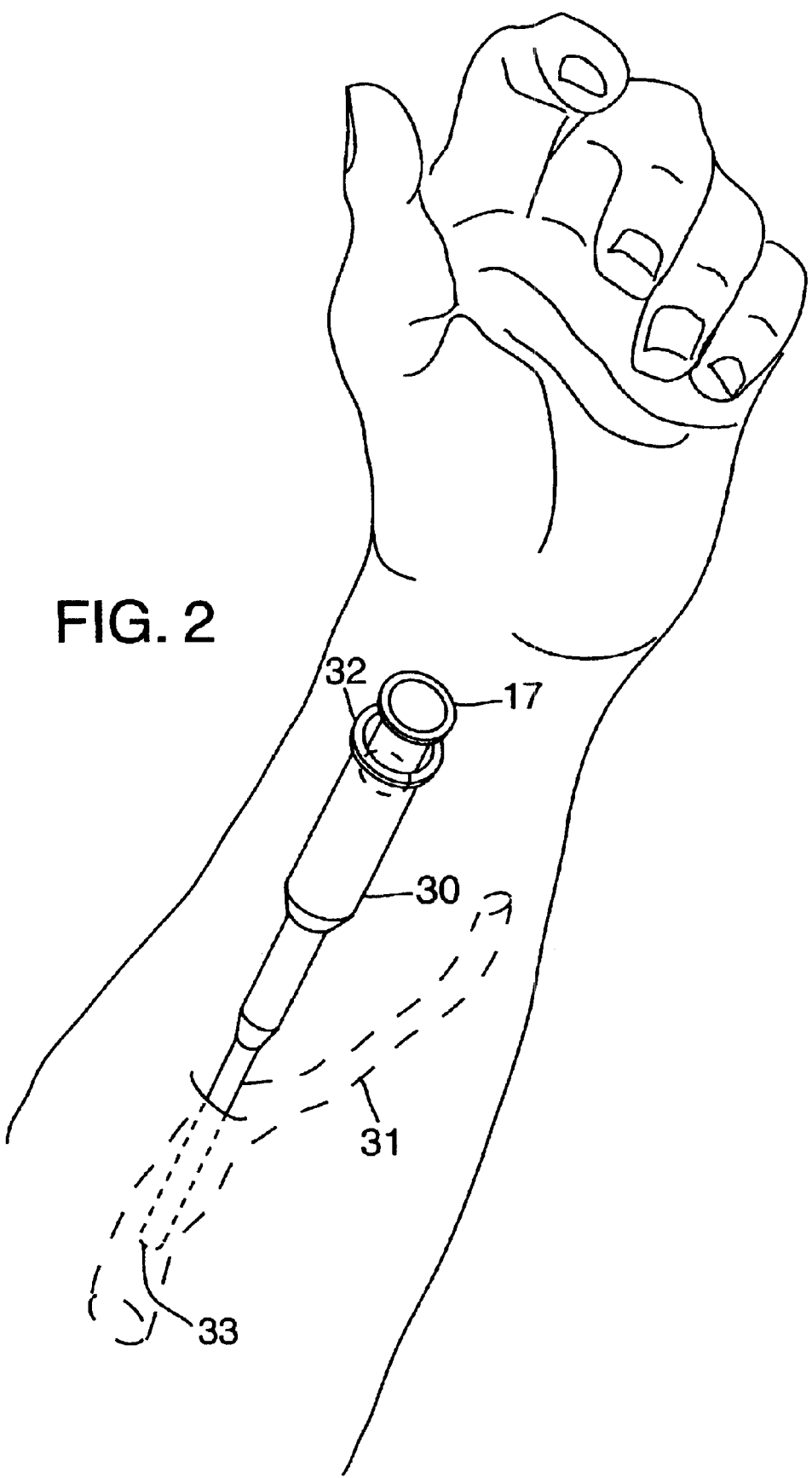
FIG. 2 shows a typical catheter inserted into a vein with a removable syringe tip inserted into the proximal end of the catheter.

FIG. 2 shows a typical vascular catheter 30 known in the art inserted in an arm vein 31. The catheter has a proximal end 32 for insertion of a syringe tip 17 and a distal end or tip 33, which resides in the lumen of the blood vessel. Syringe tip 17 is shown in this figure as an adapter which can fit over a standard syringe tip, i.e., removably attachable to a syringe tip.

Figure 3:
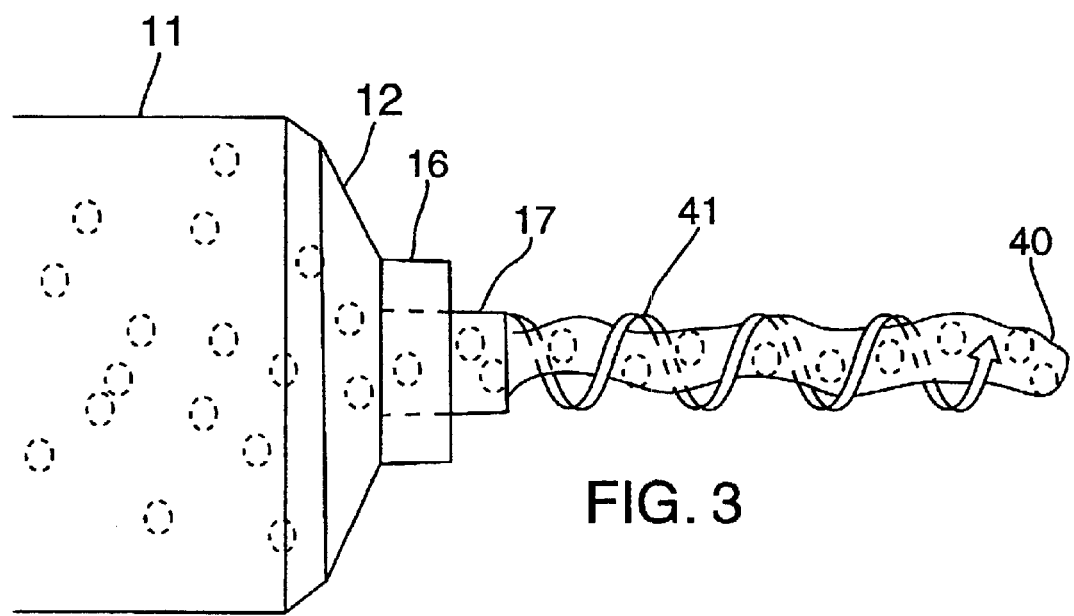
FIG. 3 illustrates the creation of helical or spiral flows of fluid as it is injected through the syringe tip of the present invention.

FIG. 3 shows flushing liquid 40 being injected out of syringe tip 17 in a spiral 41 fashion. In this figure, syringe tip 17 is shown as part of the syringe barrel 11 at distal end 12 within luer fitting 16, i.e. permanently attached.

Figure 4A:
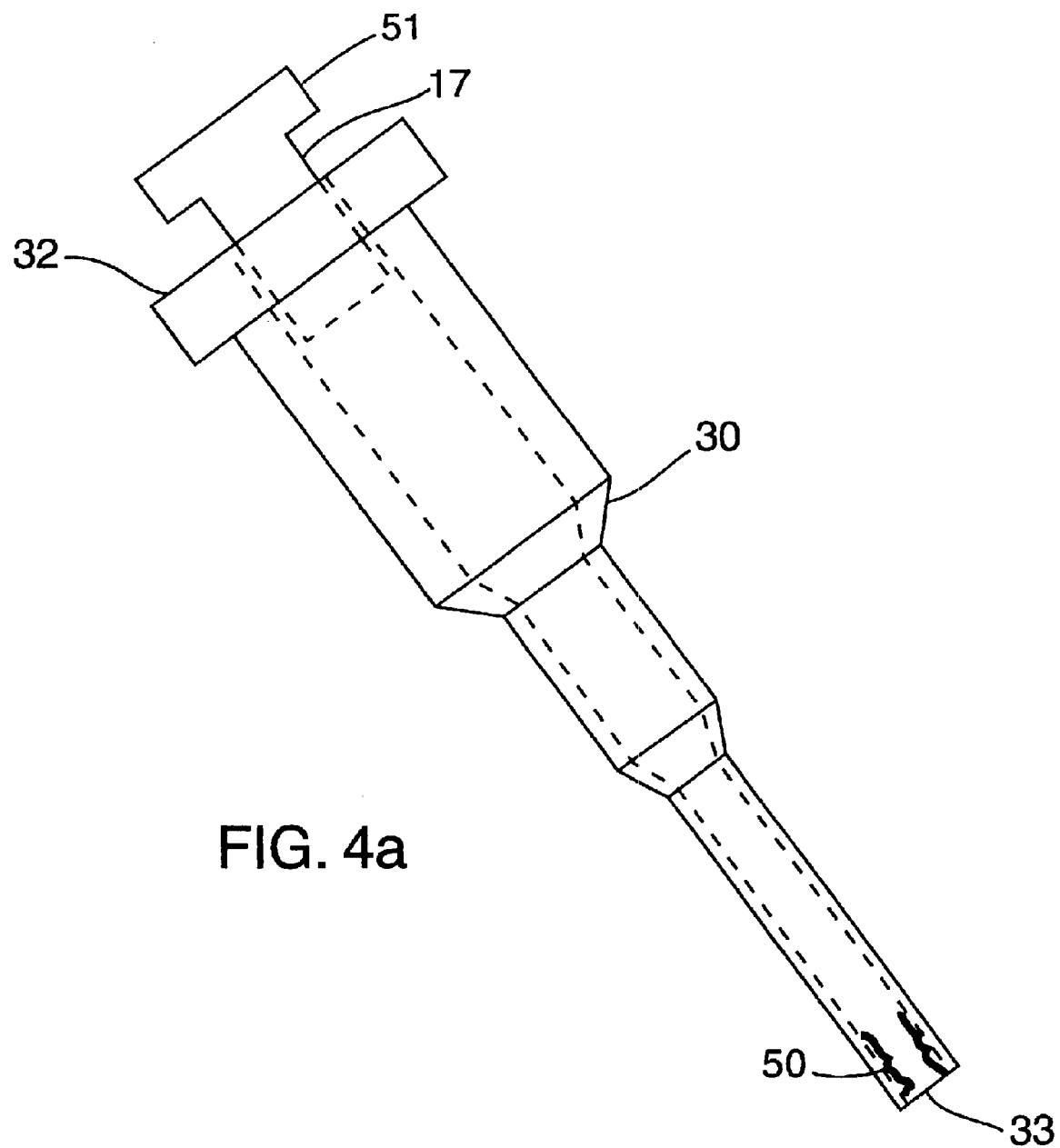
FIGS. 4a and 4b show a catheter with blood-derived deposits at the distal tip and how flushing media is flushed through the syringe tip of the present invention and flows in a controlled spiral or helical fashion down the length of the catheter to dislodge the blood-derived deposits.

FIG. 4a shows syringe tip 17 of the present invention inserted into the proximal end 32 of catheter 30. At distal end 33 of catheter 30 is shown blood-derived debris 50, which typically forms, by thrombosis at catheter tips and associated lumens after insertion into the lumen of a blood vessel. Syringe tip 17 is shown in the adapter configuration. Lip 51 of adapter 17 is constructed to fit tightly and removably over a standard syringe tip or any other device for infusing fluid such as needles, catheters, tubes, and the like. Although lip 51 is depicted as a simple annular fitting, it may be constructed in many other configurations including luer-lock fittings, needle-like fittings, and the like.

Figure 4B:
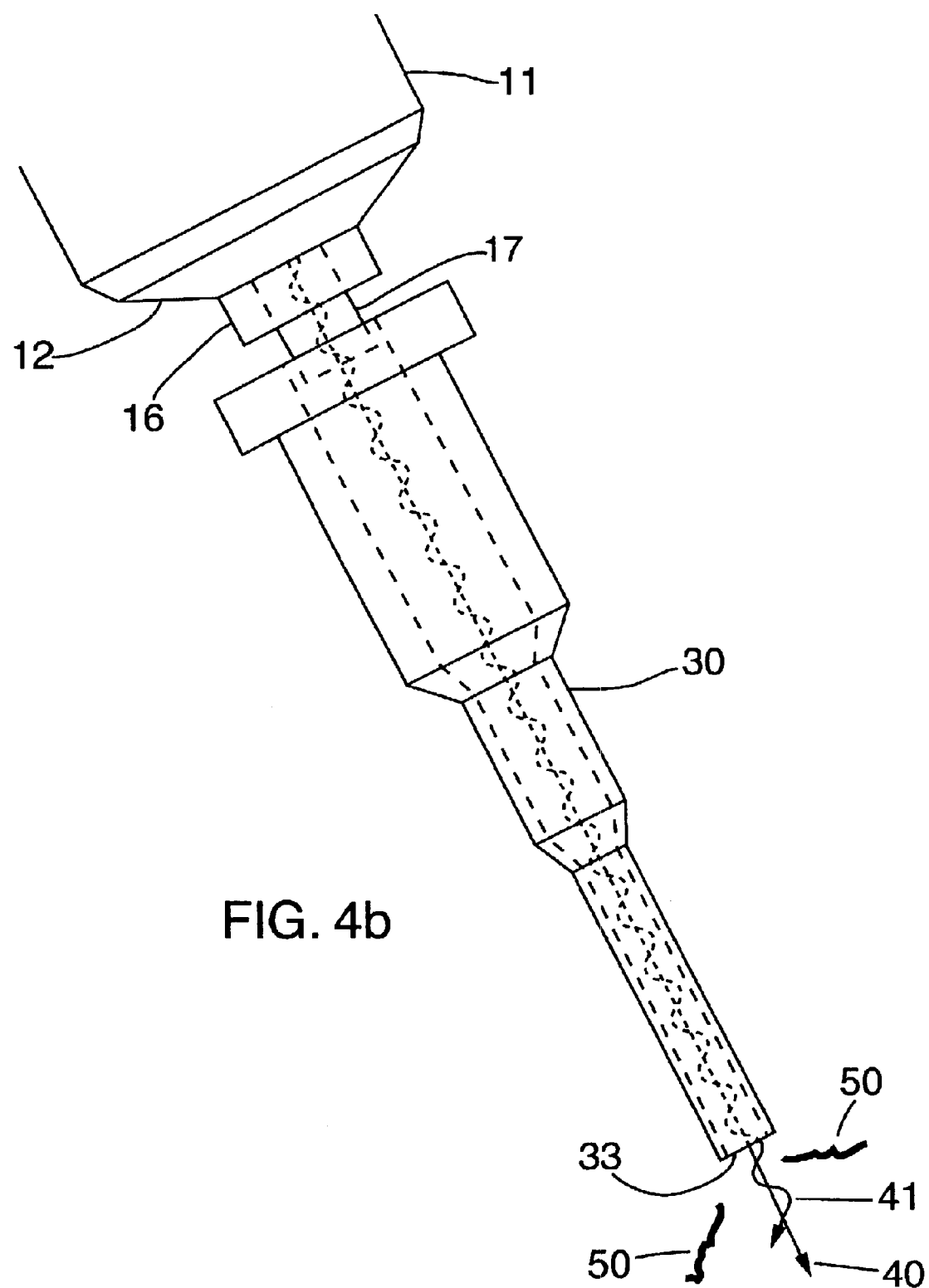

FIG. 4b shows flushing liquid 40 being injected out of syringe tip 17 through catheter 30 and out through catheter tip 33. Blood-derived debris 50 is shown as dislodged by the spiral or helical flow 41 of flushing liquid 40. Syringe tip 17 is shown as an integral permanent part of luer fitting 16 at the distal end 12 of syringe 11. With the syringe tip of the present invention it is possible to flush the catheter effectively with a single uninterrupted injection of flushing fluid and the start-stop procedure is not required.

Figure 5A:
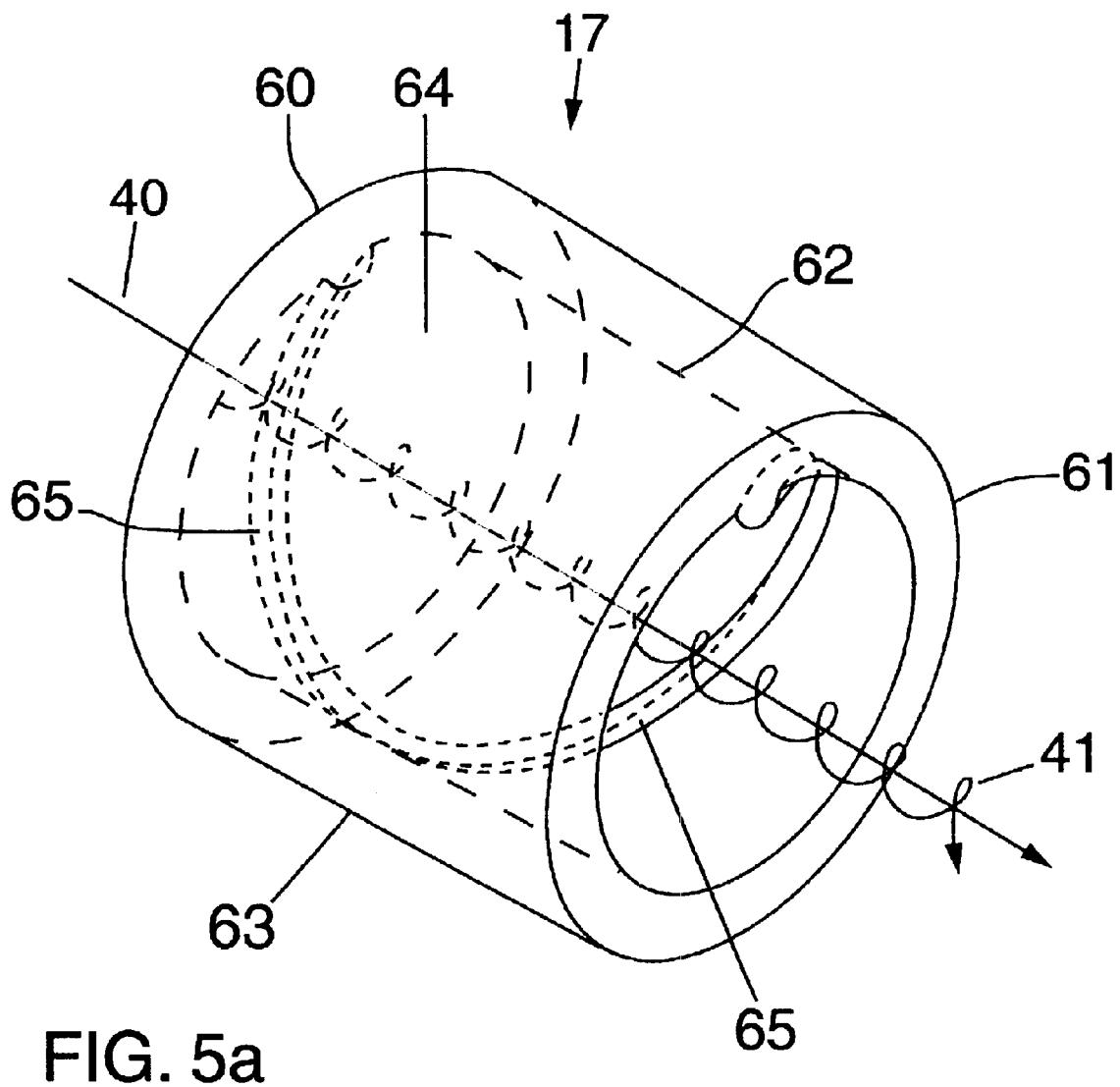
FIGS. 5a and 5b show enlarged frontal and side views of the syringe tip of the present invention illustrating the spiral or helical protruding elements on the inner surface of the syringe tip.

FIG. 5a shows a perspective view from distal end 61 of syringe tip 17. Syringe tip 17 has a proximal end 60 which will fit onto distal end 12 of a syringe, either permanently or reversibly by methods known in the art. Syringe tip 17 has a distal end 61 through which flushing fluid 40 is ejected. Syringe tip 17 has an inner surface 62, an outer surface 63, and a circular lumen 64. Outer surface 63 may be of any suitable shape; preferably circular, such that syringe tip 17 is shaped like a cylinder. The inner surface 62 of syringe tip 17 has a spiral or helical element 65 which begins at a point that is flush with proximal end 60 and ends at a point that is flush with distal end 61. This spiral element 65 twists 360E as it courses evenly and smoothly from the proximal end 60 to the distal end 61. As flushing fluid 40 is pushed through distal end 61, flushing fluid 40 is forced into a rotating, spiral, or helical flow 41. FIG. 5a shows a single spiral element 65, which protrudes from inner surface 62 into lumen 64 of syringe tip 17.

Figure 5B:
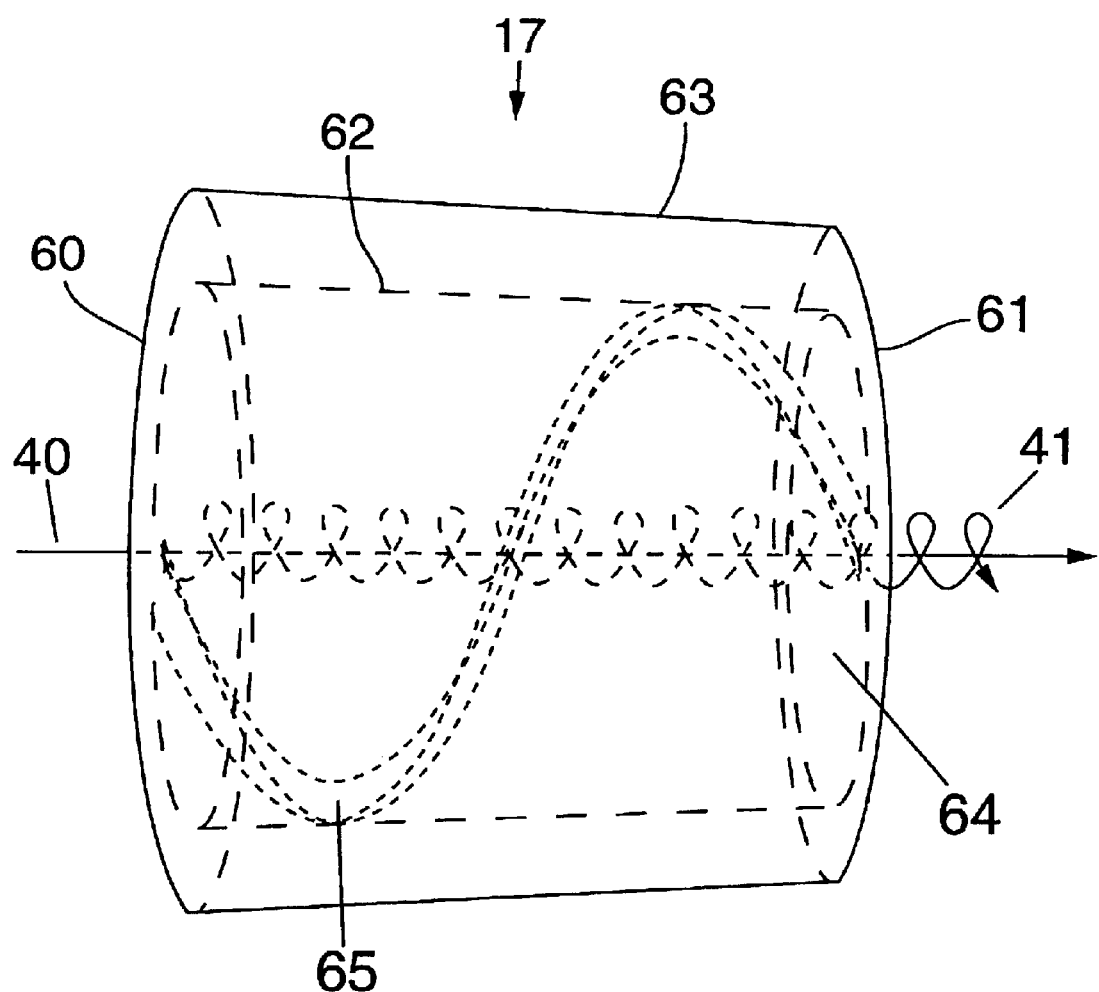
Figure 5C:
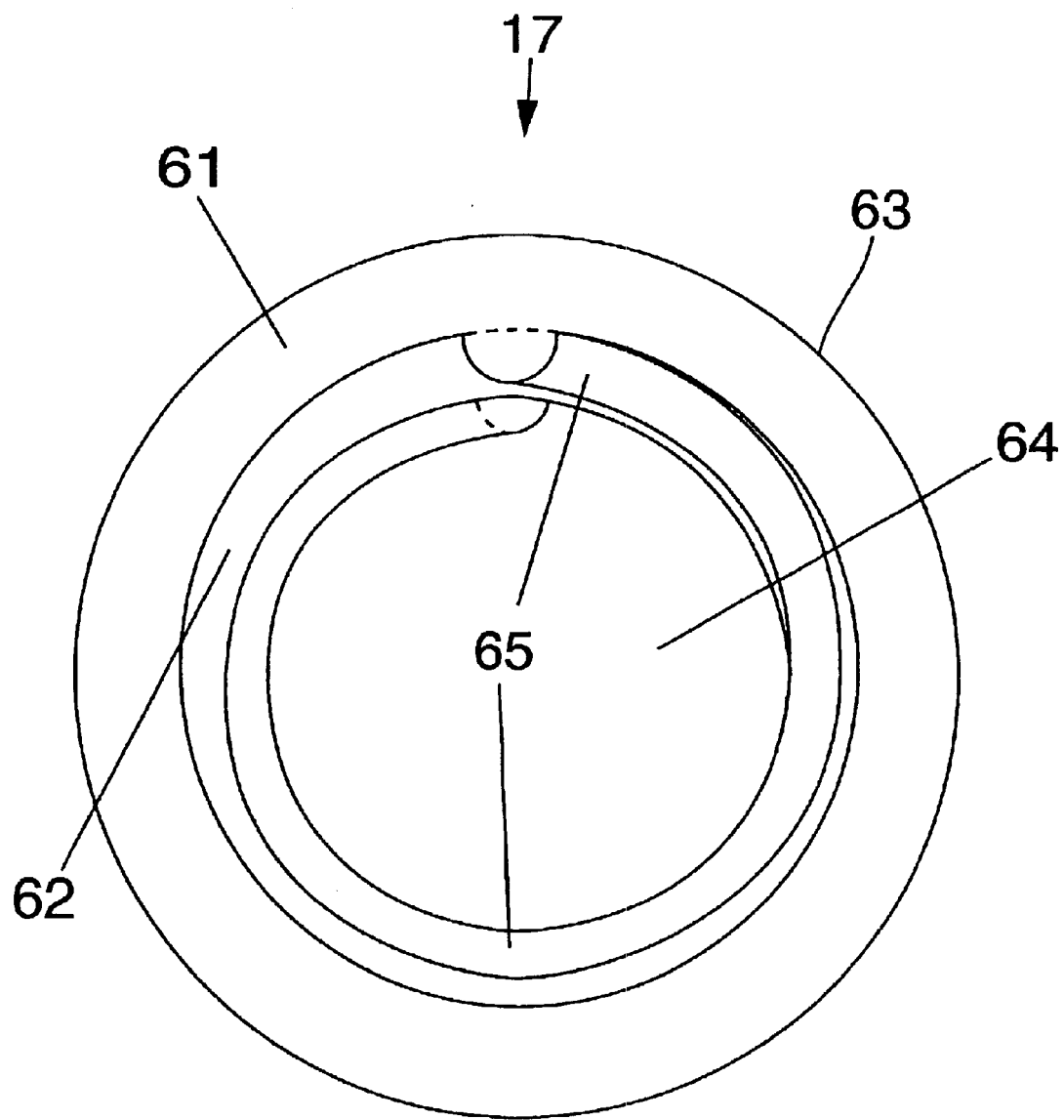
FIG. 5c shows a view of the internal lumen of the syringe tip from the distal end.

FIG. 5b shows a side view of syringe tip 17, illustrating how spiral element 65 twists 360E as it courses evenly and smoothly from proximal end 60 to distal end 61. FIG. 5c shows a view of the internal lumen 64 of syringe tip 17 from distal end 61.

Figure 6A:
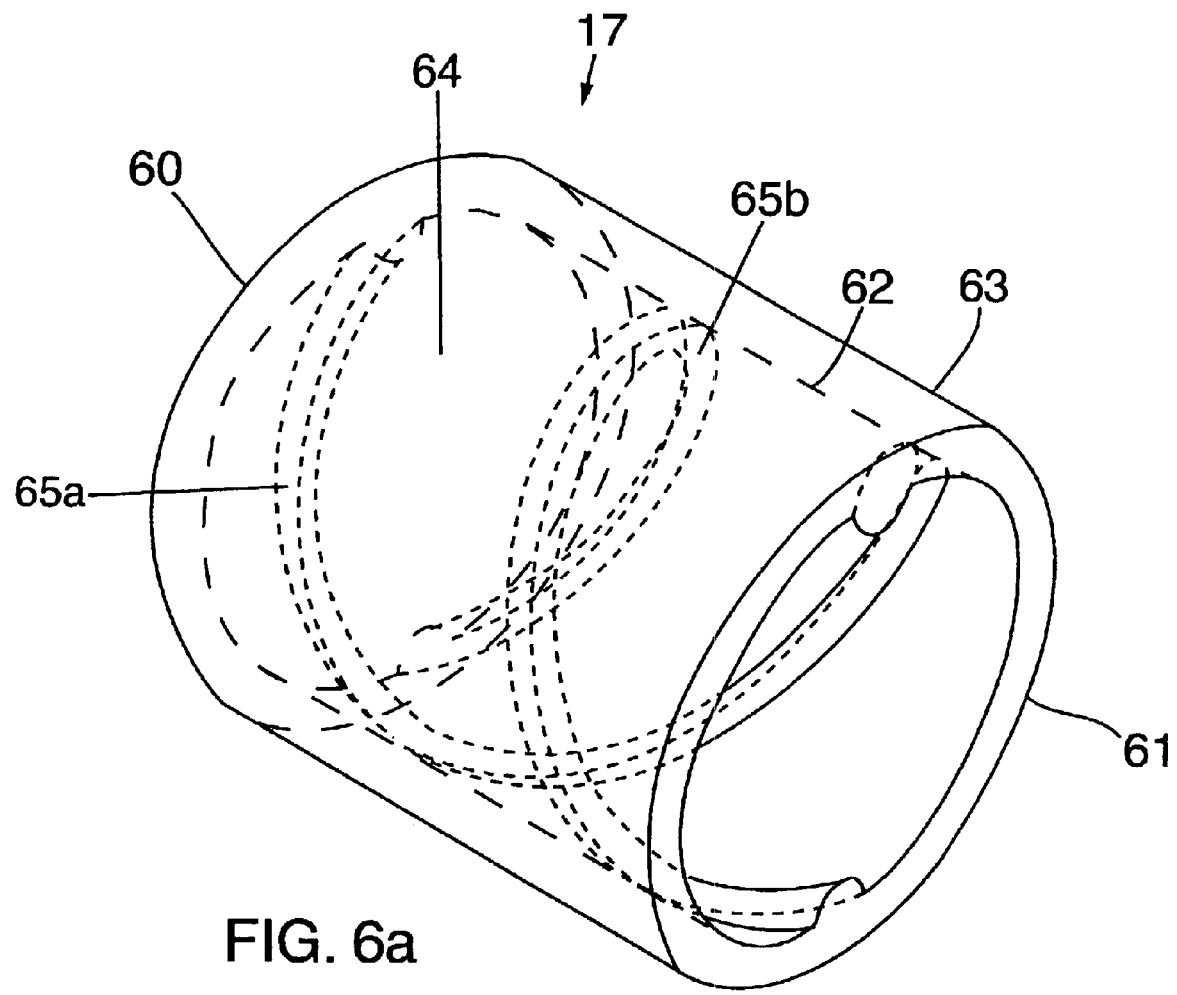
FIGS. 6a and 6b show views of syringe tips with two or three protruding spiral elements on the inner surface.
Figure 6B:
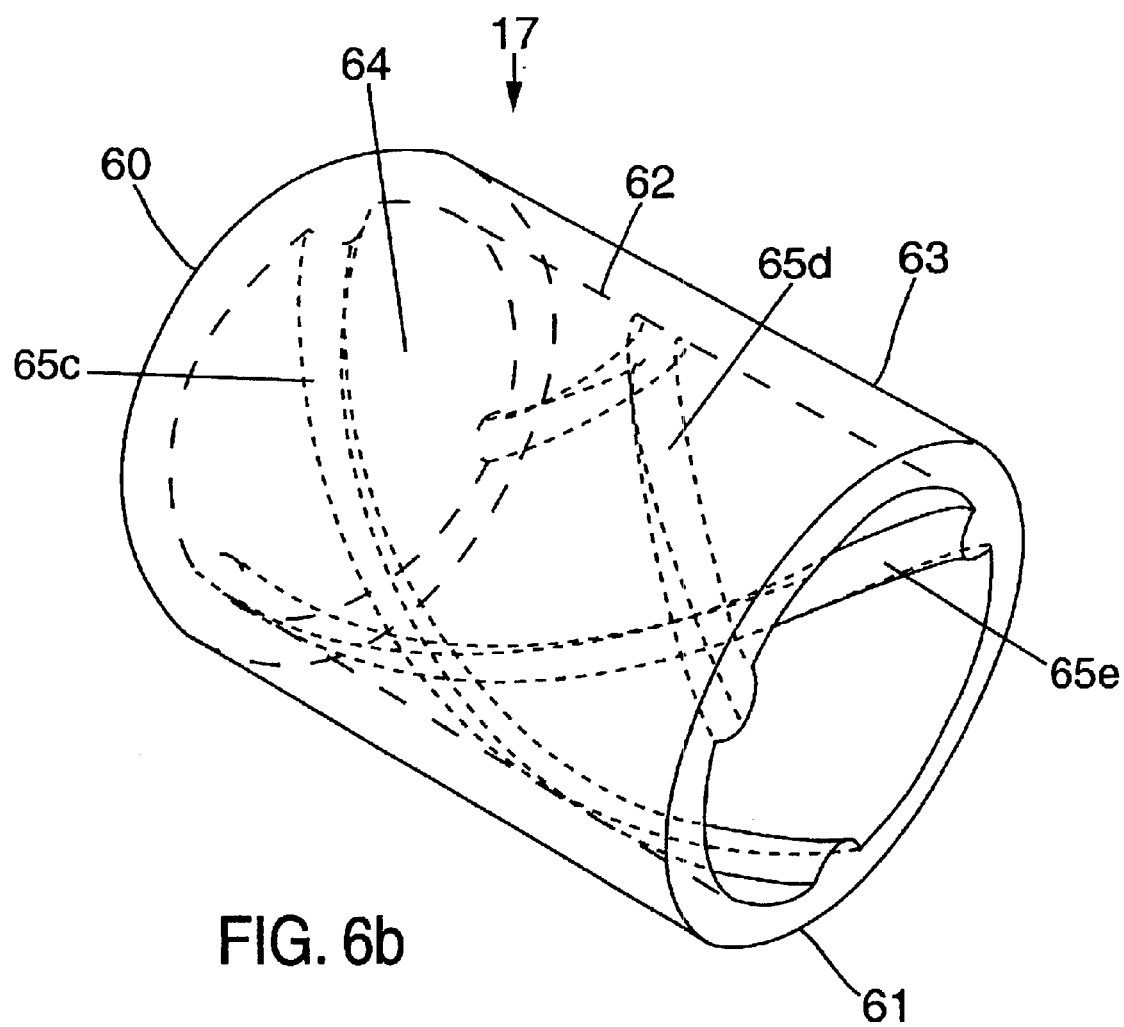
Figure 7A:
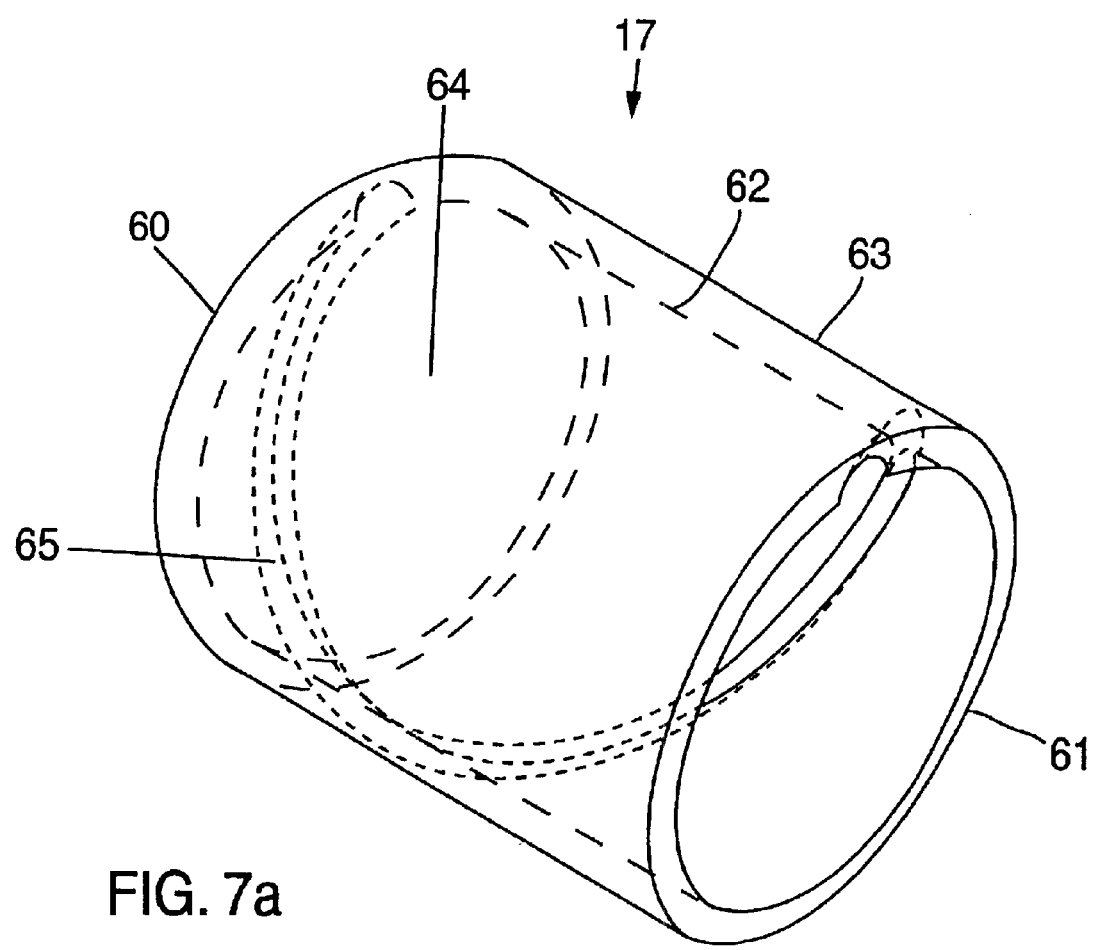
FIGS. 7a, 7b, and 7c show views of syringe tips with one, two, or three helical or spiral depressions on the inner surface.
Figure 7B:
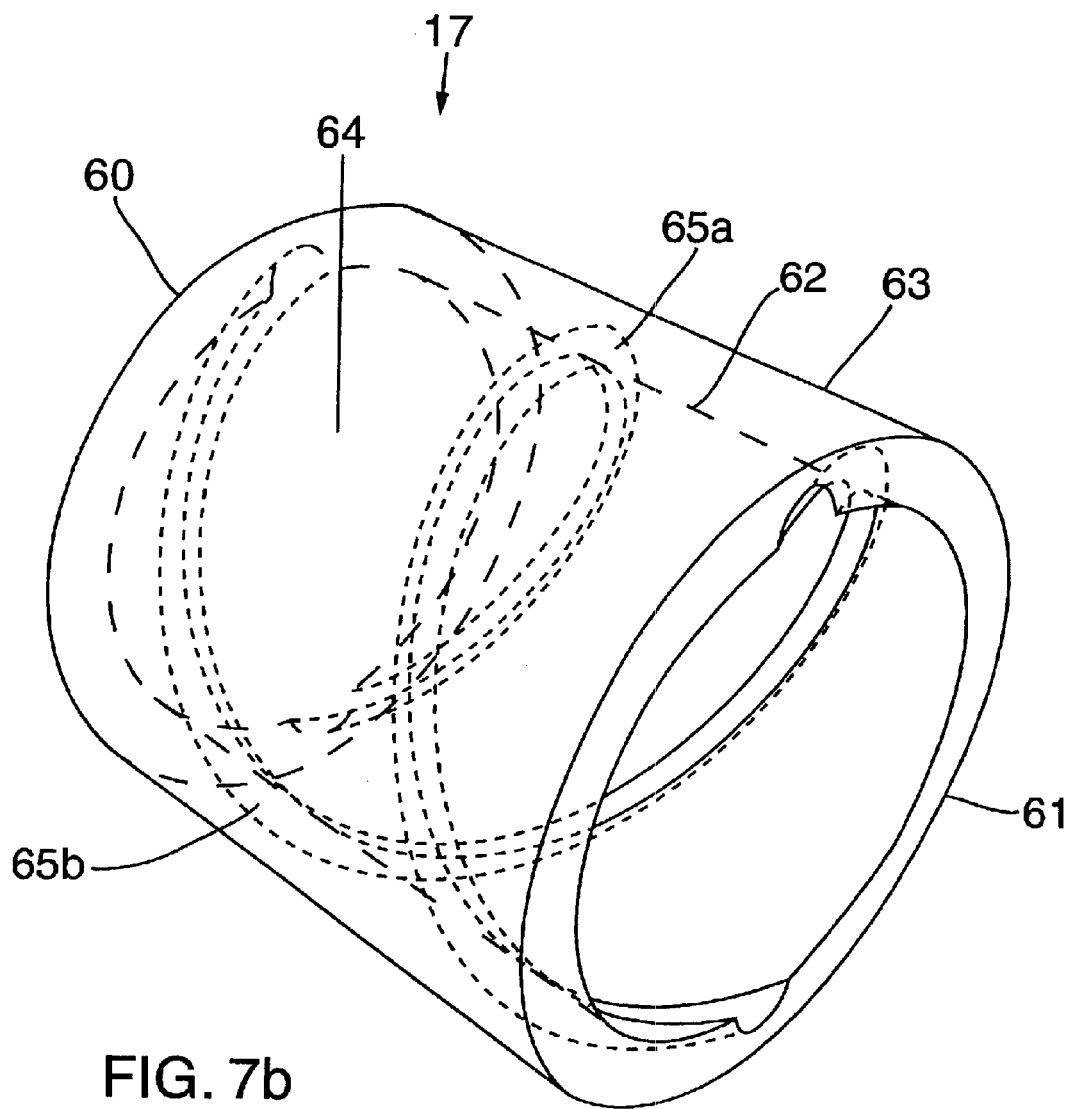
Figure 7C:
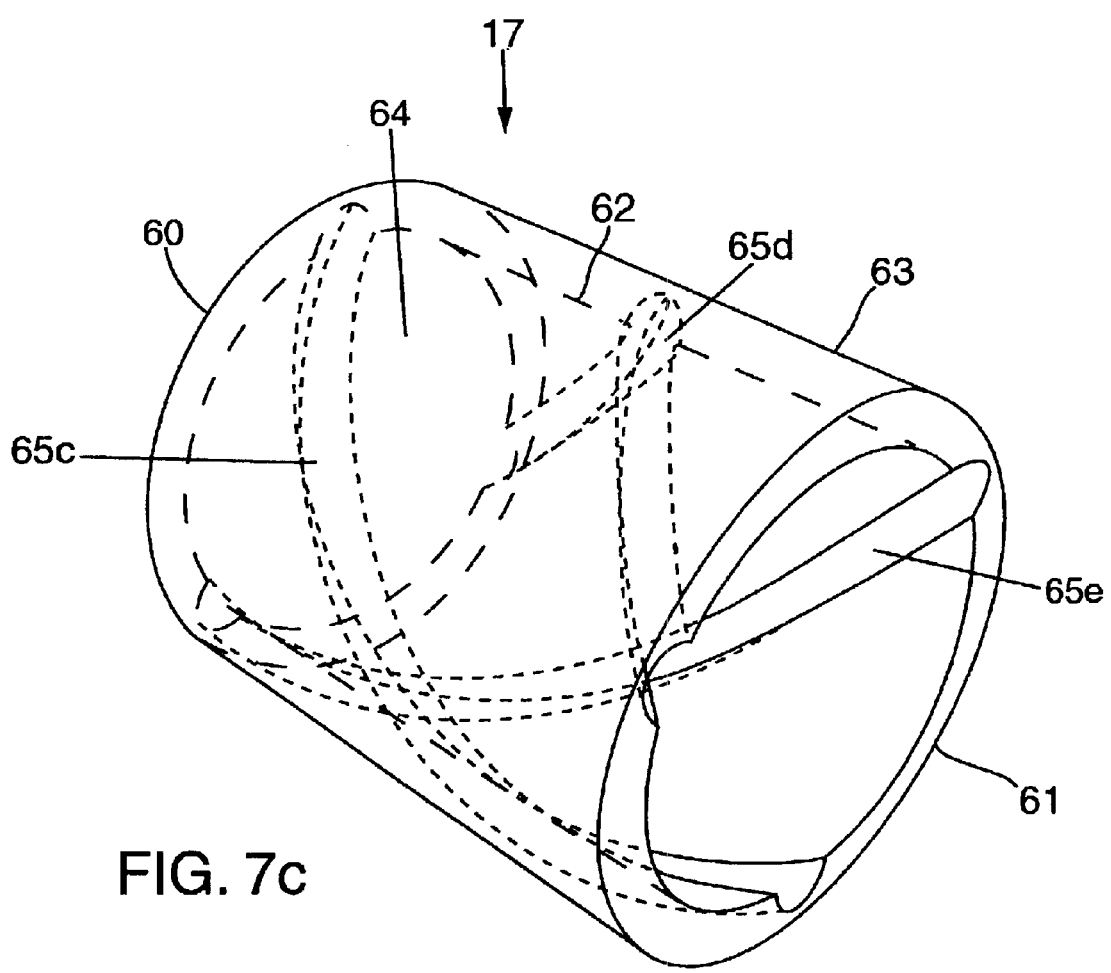

FIGS. 6a and 6b show views of syringe tip 17 with two (65a, b) or three (65c, d, e) spiral elements 65 on the inner surface 62. These spiral elements also protrude from inner surface 62 into lumen 64. Spiral elements 65 on inner surface 62 may also be indentations into inner surface 62. Spiral elements that are indentations are depicted in FIGS. 7a, 7b, and 7c where FIG. 7a shows a single spiral element 65, FIG. 7b shows two spiral elements, 65a and 65b, and FIG. 7c shows three spiral elements, 65c, 65d, and 65e.

In the examples shown in FIGS. 5a–7b the spiral elements 65 that are protrusions from the inner surface 62 into lumen 64 or indentations into inner surface 62 or a combination thereof, can be round, square, triangular, or a combination thereof, or any other suitable shape. The spiral elements may form less or more than a complete 360E turn. For example, the spirals may make only a one eighth (45E) turn or several complete turns.

Figure 8A:
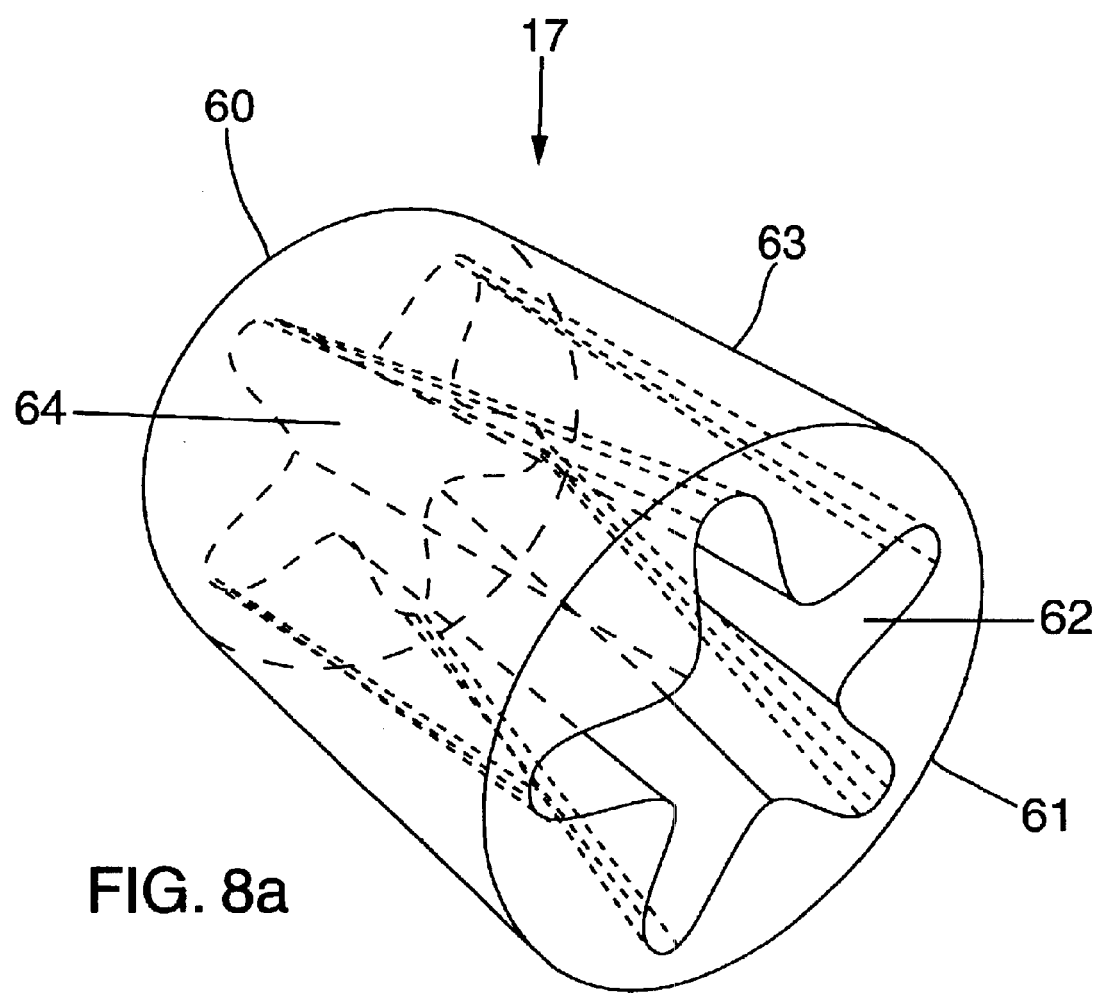
FIGS. 8a, 8b, 8c, and 8d show views of syringe tips with a star shaped bore, a twisting bisection luminal inclusion, a twisting triform luminal inclusion, and a quadraform luminal inclusion.
Figure 8B:
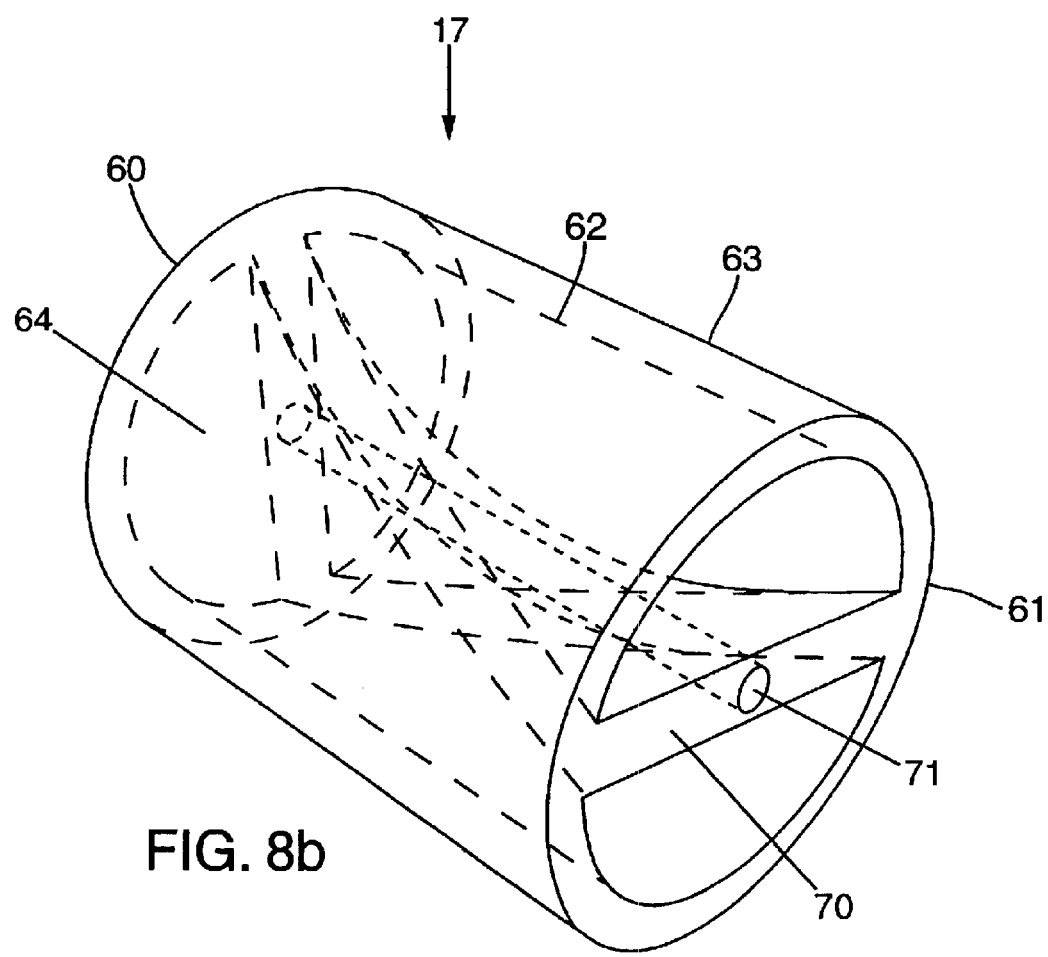
Figure 8C:
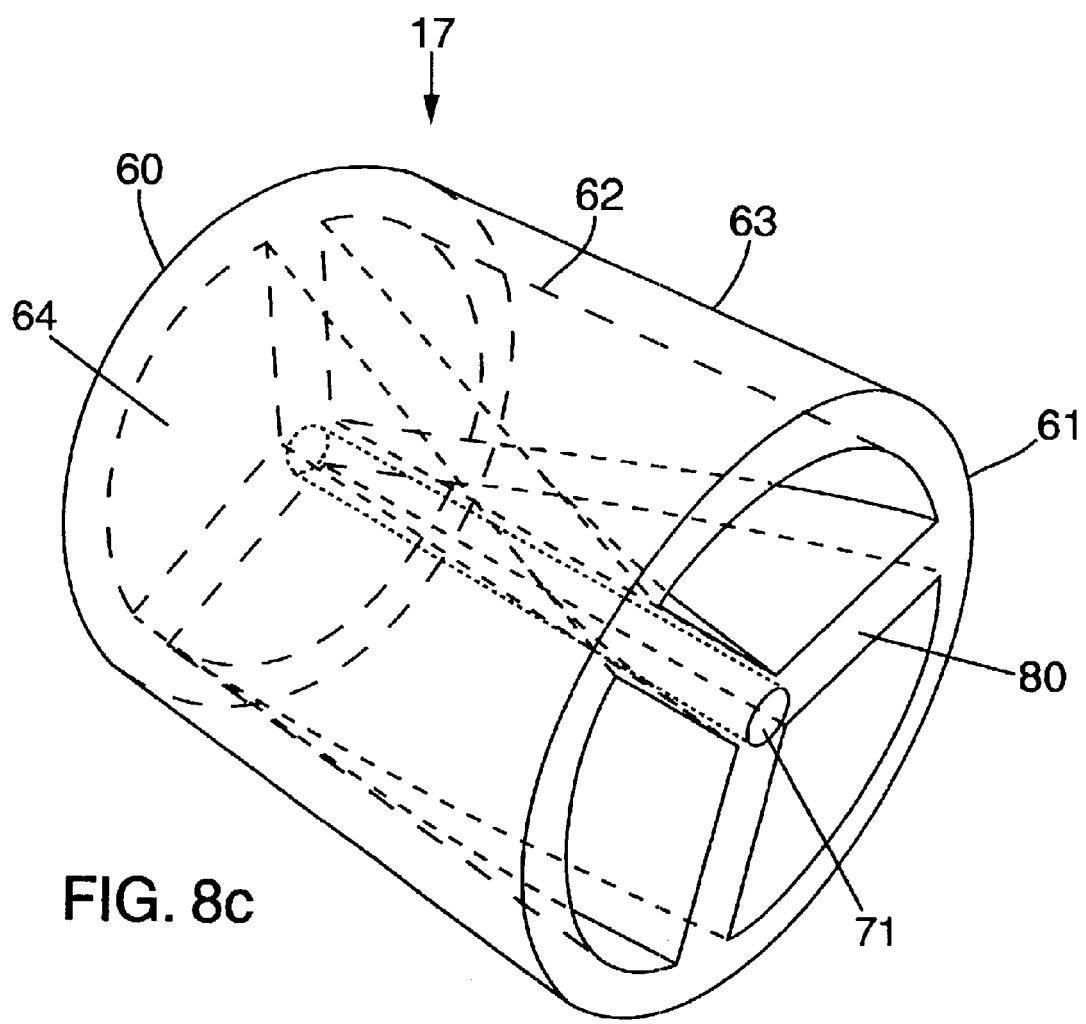
Figure 8D:
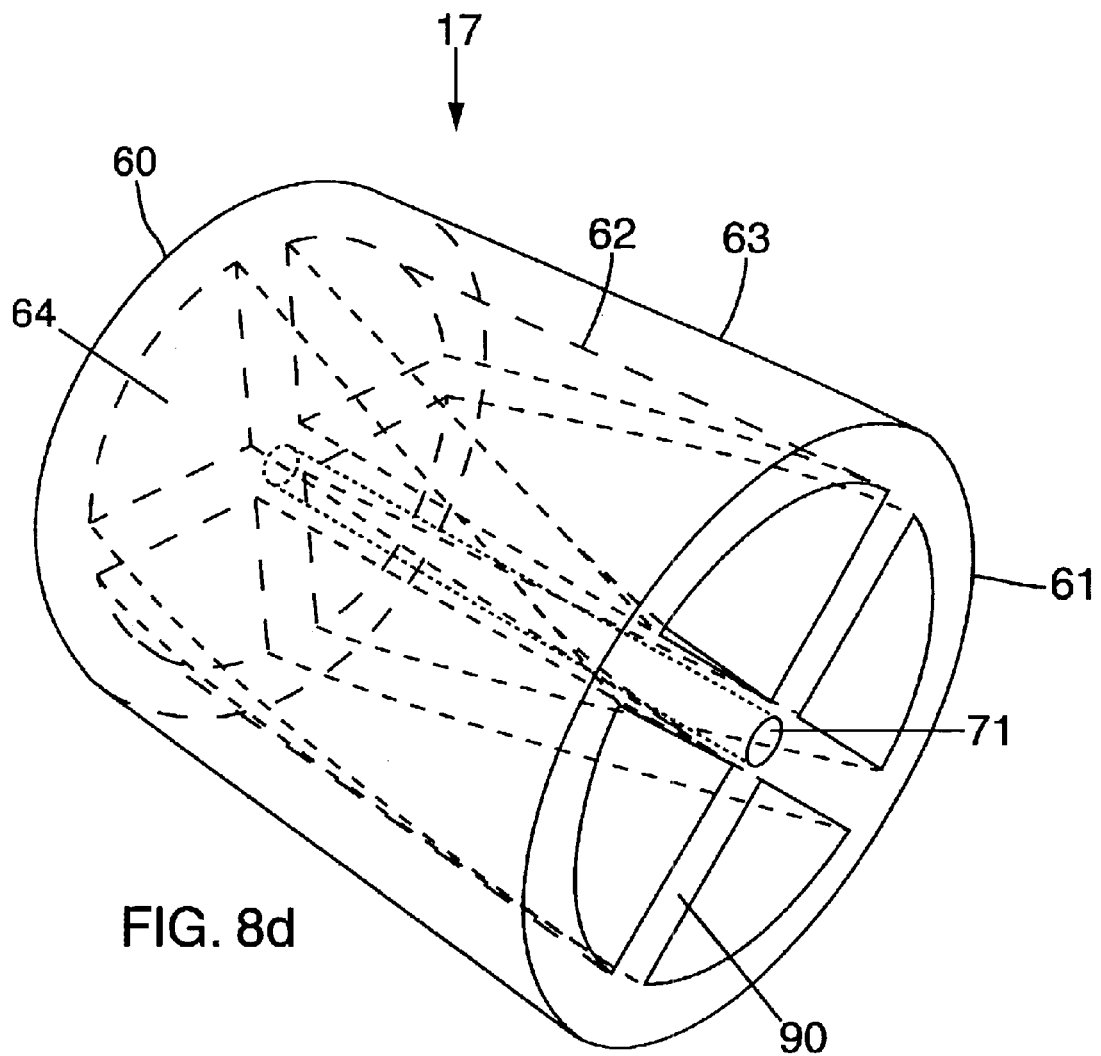

FIGS. 8a, 8b, 8c and 8d show alternate embodiments of the present invention. FIG. 8a shows syringe tip 17 wherein lumen 64 is in the shape of a five-point star which, twists or spirals from proximal end 60 to distal end 61. FIG. 8b shows syringe tip 17 with a bisection luminal inclusion 70 having a 45E twist from proximal end 60 to distal end 61. Luminal bisection 70 may also have a central discharge tube 71. FIG. 8c shows syringe tip 17 with a triform luminal 80 inclusion with a 45E degree twist from proximal end 60 to distal end 61. Triform luminal inclusion may also have central discharge tube 71. FIG. 8d show syringe tip 17 with a quadriform luminal inclusion 90 with a 45E twist and center discharge tube 71. These inclusions may also make one or more complete turns.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, the syringe tip of the present invention may be used in a variety of lengths and diameters and with other flushing devices besides syringes. The syringe tip may be made of plastic, metal, or glass. The syringe tip may be used to flush any type of indwelling tube. The syringe tip may have any external shape as desired.

It will be understood that various changes in the details, materials, and arrangements of the parts which have been described and illustrated above in order to explain the nature of this invention may be made by those skilled in the art without departing from the principle and scope of the invention as recited in the following claims.

I claim:

1. A method for flushing a vascular access device to remove blood-derived deposits, comprising the steps of:
   a) connecting a syringe tip to a vascular device;
   b) injecting flushing fluid through said syringe tip which causes a nonlaminar spiral flow of said flushing fluid;
   c) flushing said vascular access device as said nonlaminar, spiral flow moves out of said syringe tip and through said vascular access device; and
   d) said injecting being a single, uninterrupted injection of flushing fluid.

2. A method according to claim 1 wherein causing a nonlaminar spiral flow of said flushing fluid is produced by spiral elements within said syringe tip.

3. A method according to claim 2 wherein causing a nonlaminar spiral flow of said flushing fluid is produced by said flushing fluid passing through spiral indentations, or protrusions, or a combination thereof within said syringe tip.

4. A method of flushing a vascular access device comprising forcing flushing fluid through said vascular access device causing a nonlaminar spiral flow of said flushing fluid, wherein said nonlaminar spiral flow of said flushing fluid removes blood-derived deposits from said vascular access device and wherein said spiral flow of said flushing fluid is caused by a syringe tip connected to said vascular access device.

5. A method according to claim 4 wherein said forcing flushing fluid through said syringe tip is produced with a single uninterrupted injection of flushing fluid.

6. A method according to claim 5 wherein causing a nonlaminar spiral flow of said flushing fluid is produced by said spiral elements within said syringe tip.

7. A method according claim 6 wherein causing a nonlaminar spiral flow of said flushing fluid is produced by said flushing fluid passing through spiral indentations, or protrusions, or a combination thereof within said syringe tip.

* * * * *